United States Patent
Kazala, Jr. et al.

(10) Patent No.: US 10,004,880 B2
(45) Date of Patent: Jun. 26, 2018

(54) SYSTEM AND APPARATUS FOR TREATING A TISSUE SITE HAVING AN IN-LINE CANISTER

(71) Applicant: KCI Licensing, Inc., San Antonio, TX (US)

(72) Inventors: Richard Marvin Kazala, Jr., San Antonio, TX (US); Justin Alexander Long, San Antonio, TX (US); Kenneth Mitchel Knowles, Bandera, TX (US)

(73) Assignee: KCI LICENSING, INC., San Antonio, TX (US)

( * ) Notice: Subject to any disclaimer, the term of this patent is extended or adjusted under 35 U.S.C. 154(b) by 1305 days.

(21) Appl. No.: 13/653,997

(22) Filed: Oct. 17, 2012

(65) Prior Publication Data

US 2013/0096536 A1    Apr. 18, 2013

Related U.S. Application Data

(60) Provisional application No. 61/548,129, filed on Oct. 17, 2011.

(51) Int. Cl.
| | |
|---|---|
| *A61M 27/00* | (2006.01) |
| *A61M 1/00* | (2006.01) |
| *A61F 13/00* | (2006.01) |

(52) U.S. Cl.
CPC ....... *A61M 27/00* (2013.01); *A61F 13/00068* (2013.01); *A61M 1/0001* (2013.01); *A61M 1/0088* (2013.01)

(58) Field of Classification Search
CPC .. A61M 1/001; A61M 27/00; A61F 13/00068
(Continued)

(56) References Cited

U.S. PATENT DOCUMENTS

| | | | |
|---|---|---|---|
| 1,355,846 | A | 10/1920 | Rannells |
| 2,547,758 | A | 4/1951 | Keeling |

(Continued)

FOREIGN PATENT DOCUMENTS

| | | |
|---|---|---|
| AU | 550575 A1 | 3/1986 |
| AU | 745271 | 4/1999 |

(Continued)

OTHER PUBLICATIONS

International Search Report and Written Opinion for corresponding PCT/US2012/060555 dated Jan. 16, 2013.
(Continued)

*Primary Examiner* — Ariana Zimbouski

(57) ABSTRACT

A canister for use in administering reduced pressure to a tissue site includes a center body, a first end cap, and a second end cap. The center body includes a first end, second end, and a number of fluidly separate body conduits. The first end cap is connected to the first end of the center body and includes a number of return conduits fluidly connecting one body conduit to another. The first end has a port for receiving a conduit in fluid communication with the tissue site. The second end cap is connected to the second end of the center body and includes a number of return conduits fluidly connecting one body conduit to another. The second end cap has a port for receiving a conduit in fluid communication with a reduced pressure source. The fluid connection between the body conduits and the return conduits creates a continuous, tortuous pathway.

16 Claims, 10 Drawing Sheets

(58) Field of Classification Search
USPC .................................... 604/317–323, 543
See application file for complete search history.

(56) References Cited

U.S. PATENT DOCUMENTS

| | | | |
|---|---|---|---|
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielson | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt et al. | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 6,071,267 A | 6/2000 | Zamierowski | |
| 6,135,116 A | 10/2000 | Vogel et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2004/0064112 A1* | 4/2004 | Sun | 604/346 |
| 2008/0082059 A1* | 4/2008 | Fink et al. | 604/305 |
| 2009/0234266 A1* | 9/2009 | Solomon et al. | 604/6.09 |
| 2010/0125258 A1* | 5/2010 | Coulthard et al. | 604/319 |

FOREIGN PATENT DOCUMENTS

| | | |
|---|---|---|
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| EP | 1905465 A1 | 4/2008 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 B | 3/1999 |
| GB | 2 333 965 A | 8/1999 |
| JP | 4129536 | 4/1992 |
| SG | 71559 | 4/2002 |
| WO | 80/02182 | 10/1980 |
| WO | 87/04626 | 8/1987 |
| WO | 90/010424 | 9/1990 |
| WO | 93/09727 | 5/1993 |
| WO | 94/020041 | 9/1994 |
| WO | 96/05873 | 2/1996 |
| WO | 97/18007 | 5/1997 |
| WO | 99/13793 | 3/1999 |
| WO | WO2005086879 A2 | 9/2005 |
| WO | 2009002260 A1 | 12/2008 |
| WO | WO2009002260 A1 | 12/2008 |
| WO | 2009068667 A2 | 6/2009 |
| WO | WO2009068667 A2 | 6/2009 |

OTHER PUBLICATIONS

N.A. Bagautdinov, "Variant of External Vacuum Aspiration in the Treatment of Purulent Diseases of the Soft Tissues," Current Problems in Modern Clinical Surgery: Interdepartmental Collection,

(56) References Cited

OTHER PUBLICATIONS edited by V. Ye Volkov et al. (Chuvashia State University, Cheboksary, U.S.S.R. 1986);pp. 94-96 (certified translation).
Louis C. Argenta, MD and Michael J. Morykwas, PhD; "Vacuum-Assisted Closure: A New Method for Wound Control and Treatment: Animal Studies & Basic Foundation"; Annals of Plastic Surgery, vol. 38, No. 6, Jun. 1997; pp. 553-562.
Susan Mendez-Eastmen, RN; "When Wounds Won't Heal" RN Jan. 1998, vol. 61 (1); Medical Economics Company, Inc., Montvale, NJ, USA; pp. 20-24.
James H. Blackburn, II, MD, et al; "Negative-Pressure Dressings as a Bolster for Skin Grafts"; Annals of Plastic Surgery, vol. 40, No. 5, May 1998, pp. 453-457.
John Masters; "Reliable, Inexpensive and Simple Suction Dressings"; Letters to the Editor, British Journal of Plastic Surgery, 1998, vol. 51 (3), p. 267; Elsevier Science/The British Association of Plastic Surgeons, UK.
S.E. Greer, et al "The Use of Subatmospheric Pressure Dressing Therapy to Close Lymphocutaneous Fistulas of the Groin" British Journal of Plastic Surgery (2000), vol. 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, vol. 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu. N., et al; "Active Wound Drainage", Vestnik Khirurgi, vol. 138, Issue 4, 1987, and 7 page English translation thereof.
Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.
Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, p. 1.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., vol. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovic, V. Ðukić, Ž. Maksimović, Ð. Radak, and P. Peška, "Vacuum Therapy in the Treatment of Peripheral Blood Vessels," Timok Medical Journal 11 (1986), pp. 161-164 (certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, "An Improved Sump Drain-Irrigation Device of Simple Construction," Archives of Surgery 105 (1972) pp. 511-513.
C.E. Tennant, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians (Jul. 2007).
Australian Patent Examination Report No. 1 corresponding to AU2112326235 dated Jul. 27, 2016.

* cited by examiner

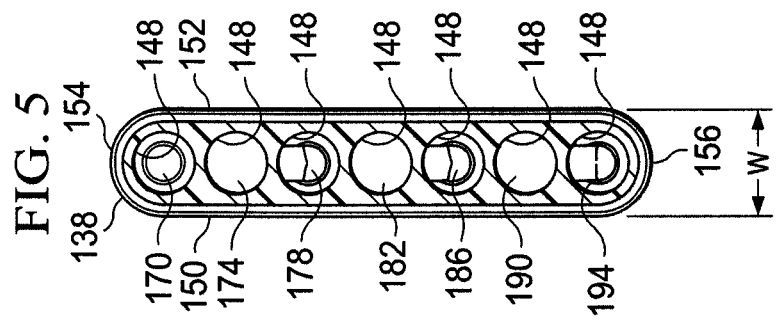
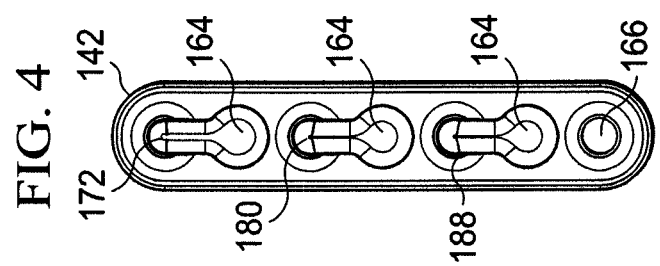
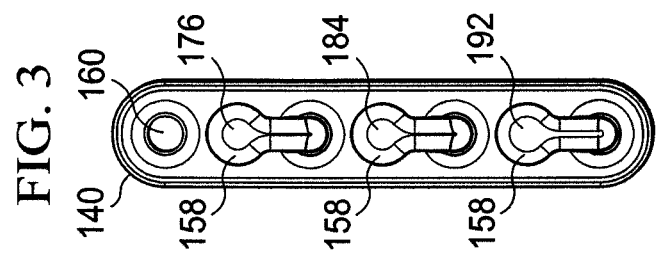

SYSTEM AND APPARATUS FOR TREATING A TISSUE SITE HAVING AN IN-LINE CANISTER

CROSS-REFERENCE TO RELATED APPLICATION

This application claims priority to U.S. Provisional Patent Application No. 61/548,129 filed Oct. 17, 2011, entitled SYSTEM AND APPARATUS FOR TREATING A TISSUE SITE HAVING AN IN-LINE CANISTER, the disclosure of which is hereby incorporated by reference in its entirety.

BACKGROUND OF THE INVENTION

Field of the Invention

The present invention relates generally to reduced pressure treatment systems and more particularly to a system and apparatus for treating a tissue site having an in-line canister.

Description of Related Art

Clinical studies and practice have shown that providing a reduced pressure in proximity to a tissue site augments and accelerates the growth of new tissue at the tissue site. The applications of this phenomenon are numerous, but one particular application of reduced pressure involves treating wounds. This treatment (frequently referred to in the medical community as "negative pressure wound therapy," "reduced pressure therapy," or "vacuum therapy") provides a number of benefits, including migration of epithelial and subcutaneous tissues, improved blood flow, and micro-deformation of tissue at the wound site Together these benefits result in increased development of granulation tissue and faster healing times. Typically, reduced pressure is applied by a reduced pressure source to tissue through a porous pad or other manifold device. The porous pad contains cells or pores that are capable of distributing reduced pressure to the tissue and channeling fluids that are drawn from the tissue. The porous pad often is incorporated into a dressing having other components that facilitate treatment.

SUMMARY

The problems presented by existing reduced pressure treatment systems are solved by the systems and methods of the illustrative embodiments described herein. In one illustrative embodiment, a canister for use in administering reduced pressure to a tissue site includes a center body, a first end cap, and a second end cap. The center body has a first end, a second end, and a number of fluidly separate body conduits extending from the first end to the second end. The first end cap is connected to the first end of the center body and has a number of return conduits configured to fluidly connect one of the body conduits with another of the body conduits. The first end cap further has a port for receiving a conduit in fluid communication with the tissue site. The second end cap is connected to the second end of the center body and has a number of return conduits configured to fluidly connect one of the body conduits with another of the body conduits. The second end cap further has a port for receiving a conduit in fluid communication with a reduced pressure source. The fluid connection between the body conduits and the return conduits of the first and second end caps creates a continuous, tortuous pathway.

In another illustrative embodiment, a canister for use in administering reduced pressure to a tissue site includes a center body, a first end cap and a second end cap. The center body has a first end, a second end, and a number of fluidly separate body conduits extending from the first end to the second end. An absorbent material is positioned in each of the number of fluidly separate body conduits. The first end cap is connected to the first end of the center body, and the first end cap has an inlet port, an outlet port, and a first plenum for receiving fluids. The second end cap is connected to the second end of the center body and has a second plenum for receiving fluids.

In yet another illustrative embodiment, a system for use in administering reduced pressure to a tissue site includes a reduced-pressure dressing, an in-line canister, and a reduced-pressure treatment unit. The reduced-pressure dressing is positioned proximate the tissue site and includes a manifold positioned within the tissue site for delivering reduced pressure to the tissue site. The in-line canister is fluidly connected to the reduced-pressure dressing through a first conduit and is operable to receive and store fluid received from the tissue site. The in-line canister includes a center body, a first end cap, and a second end cap. The center body has a first end, a second end, and a number of fluidly separate body conduits extending from the first end to the second end. The first end cap is connected to the first end of the center body and has a number of return conduits configured to fluidly connect one of the body conduits with another of the body conduits. The first end cap further has a port for receiving a conduit in fluid communication with the tissue site. The second end cap is connected to the second end of the center body and has a number of return conduits configured to fluidly connect one of the body conduits with another of the body conduits. The second end cap further has a port for receiving a conduit in fluid communication with a reduced pressure source. The fluid connection between the body conduits and the return conduits of the first and second end caps creates a continuous, tortuous pathway. The reduced-pressure treatment unit is fluidly connected to the canister through a second conduit and includes a reduced pressure source for providing reduced pressure to the tissue site.

Other objects, features, and advantages of the illustrative embodiments will become apparent with reference to the drawings and detailed description that follow.

BRIEF DESCRIPTION OF THE DRAWINGS

FIG. 3 illustrates a front view of a first end cap of the canister shown in FIG. 2 taken along line 3-3;

FIG. 4 illustrates a back view of a second end cap of the canister shown in FIG. 2 taken along line 4-4;

FIG. 5 illustrates a cross-sectional view of the center body of the canister shown in FIG. 2 taken along line 5-5;

DETAILED DESCRIPTION OF ILLUSTRATIVE EMBODIMENTS

In the following detailed description of several illustrative embodiments, reference is made to the accompanying drawings that form a part hereof, and in which is shown by way of illustration specific preferred embodiments in which the invention may be practiced. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments are defined only by the appended claims. Unless otherwise indicated, as used herein, "or" does not require mutual exclusivity.

The term "reduced pressure" as used herein generally refers to a pressure less than the ambient pressure at a tissue site that is being subjected to treatment. In most cases, this reduced pressure will be less than the atmospheric pressure at which the patient is located. Alternatively, the reduced pressure may be less than a hydrostatic pressure associated with tissue at the tissue site. Although the terms "vacuum" and "negative pressure" may be used to describe the pressure applied to the tissue site, the actual pressure reduction applied to the tissue site may be significantly less than the pressure reduction normally associated with a complete vacuum. Reduced pressure may initially generate fluid flow in the area of the tissue site. As the hydrostatic pressure around the tissue site approaches the desired reduced pressure, the flow may subside, and the reduced pressure is then maintained. Unless otherwise indicated, values of pressure stated herein are gauge pressures. Similarly, references to increases in reduced pressure typically refer to a decrease in absolute pressure, while decreases in reduced pressure typically refer to an increase in absolute pressure.

Figure 1:
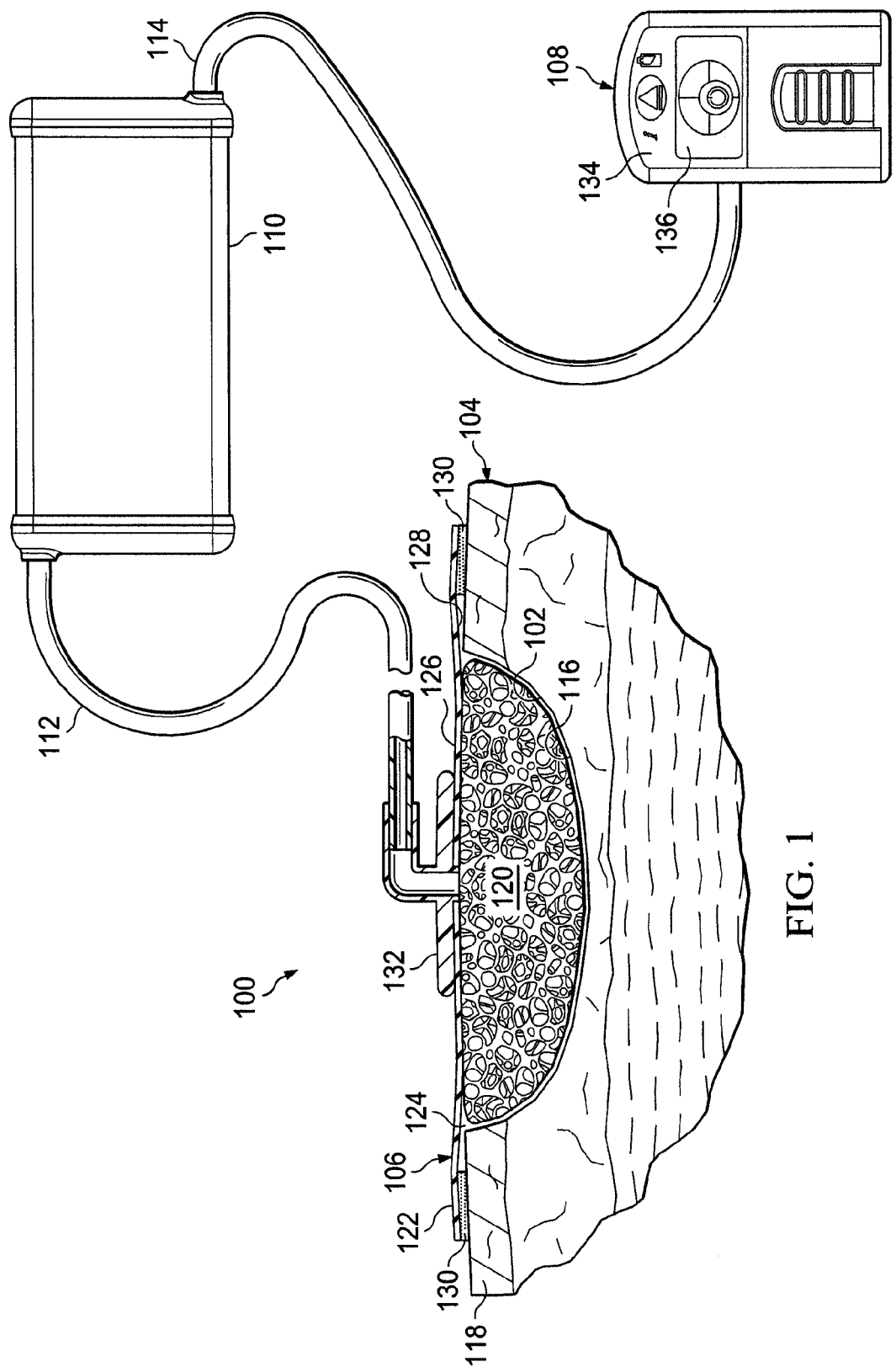
FIG. 1 illustrates a perspective view, with a portion shown in cross section, of an illustrative embodiment of a system for treating a tissue with reduced pressure.
Figure 2:
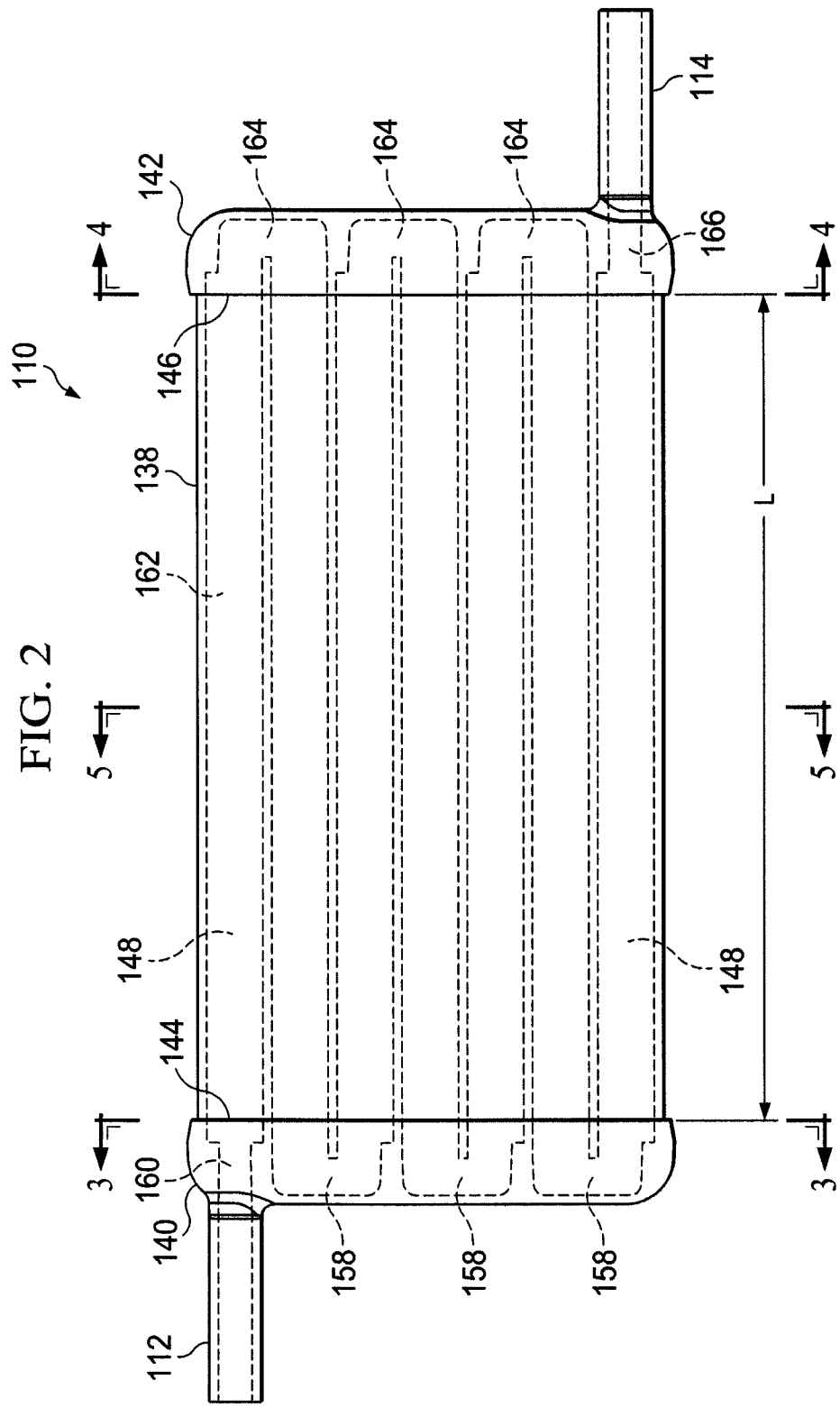
FIG. 2 illustrates a side view of an illustrative embodiment of a canister for use in the system shown in FIG. 1.

Referring to FIG. 1, an illustrative embodiment of a system 100 for treating a tissue site 102 on a patient 104 with reduced pressure is presented. The system 100 includes a reduced-pressure dressing 106 for disposing proximate the tissue site 102 and a reduced-pressure treatment unit 108 fluidly connected to the reduced-pressure dressing 106 for applying reduced pressure to the tissue site 102. The system 100 further includes a canister 110 fluidly connected to both the reduced-pressure dressing 106 and the reduced-pressure treatment unit 108. A first conduit 112 connects the reduced-pressure dressing 106 to the canister 110, and a second conduit 114 connects the reduced-pressure treatment unit 108 to the canister 110. The canister 110 is operable to receive and store fluids, including exudate, received from the tissue site 102. The canister 110 is configured to create a tortuous flow path for any fluids received from the tissue site 102. There are several potential advantages to having an in-line canister positioned between a tube set and configured to create a tortuous flow path. For example, the configuration may allow for a smaller and more discrete vacuum device and more efficient absorption of the wound exudates. The volumetric size of the canister may be increased with virtually no impact to the size of the vacuum device.

The system 100 may be used with various types of tissue sites 102. As used herein, the term "tissue site" may refer to a wound, such as a wound 116, or defect located on or within any tissue, including but not limited to, bone tissue, adipose tissue, muscle tissue, neural tissue, dermal tissue, vascular tissue, connective tissue, cartilage, tendons, or ligaments. The term "tissue site" may further refer to areas of any tissue that are not necessarily wounded or defective, but are instead areas in which it is desired to add or promote the growth of additional tissue. For example, reduced pressure tissue treatment may be used in certain tissue areas to grow additional tissue that may be harvested and transplanted to another tissue location. The wound 116 may be through an epidermis 118 and into a subcutaneous tissue or any other tissue. Treatment of the tissue site 102 may include removal of fluids, e.g. exudate or ascites.

The reduced-pressure dressing 106 may include a manifold 120 positioned proximate the tissue site 102. The manifold 120 typically includes a plurality of flow channels or pathways that distribute fluids provided to and removed from the tissue site 102 around the manifold 120. In one illustrative embodiment, the flow channels or pathways are interconnected to improve distribution of fluids provided or removed from the tissue site 102. The manifold 120 may be a biocompatible material that is capable of being placed in contact with the tissue site 102 and distributing reduced pressure to the tissue site 102. Examples of the manifold 120 may include, without limitation, devices that have structural elements arranged to form flow channels, such as, for example, cellular foam, open-cell foam, porous tissue collections, liquids, gels, and foams that include, or cure to include, flow channels. The manifold 120 may be porous and may be made from foam, gauze, felted mat, or any other material suited to a particular biological application. In one embodiment, the manifold 120 is a porous foam and includes a plurality of interconnected cells or pores that act as flow channels. The porous foam may be a polyurethane, open-cell, reticulated foam such as GranuFoam® material manufactured by Kinetic Concepts, Incorporated of San Antonio, Tex. In some situations, the manifold 120 may also be used to distribute fluids such as medications, antibacterials, growth factors, and various solutions to the tissue site 102. Other layers may be included in or on the manifold 120, such as absorptive materials, wicking materials, hydrophobic materials, and hydrophilic materials.

In one illustrative embodiment, the manifold 120 may be constructed from bioresorbable materials that do not have to be removed from a patient's body following use of the system 100. Suitable bioresorbable materials may include, without limitation, a polymeric blend of polylactic acid (PLA) and polyglycolic acid (PGA). The polymeric blend may also include without limitation polycarbonates, polyfumarates, and capralactones. The manifold 120 may further serve as a scaffold for new cell-growth, or a scaffold material may be used in conjunction with the manifold 120 to promote cell-growth. A scaffold is a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

The reduced-pressure dressing 106 may further include a cover or drape 122 positioned over the manifold 120 to secure the manifold 120 at the tissue site 102 and to create a sealed space 124 over the tissue site 102. The drape 122 has a first side 126, and a second, tissue-facing side 128. The drape 122 may be any material that provides a fluid seal adequate to maintain reduced pressure at a desired site given the particular reduced-pressure source or subsystem involved. The drape 122 may, for example, be an impermeable or semi-permeable, elastomeric material.

An attachment device 130 may be used to hold the drape 122 against a portion of the patient's intact epidermis 118 or another layer, such as a gasket or additional sealing member. The attachment device 130 may take numerous forms. For example, the attachment device 130 may be a medically acceptable adhesive or bonding agent, such as a pressure-sensitive adhesive, that extends about a periphery or all of the drape 122. The attachment device 130 may also be a sealing ring or other device. The attachment device 130 is disposed on the second, tissue-facing side 128 of the drape 122. Before use, the attachment device 130 may be covered by a release liner (not shown).

In another embodiment, a seal layer (not shown) such as, for example, a hydrogel or other material may be disposed between the drape 122 and the epidermis 118 to augment or substitute for the sealing properties of the attachment device 130. In one embodiment, the drape 122 and the bonding characteristics of the drape 122 provide sealing sufficient to prevent leakage greater than 0.5 L/min at 125 mmHg reduced pressure.

The reduced-pressure dressing 106 may further include a reduced-pressure interface 132 positioned adjacent to or coupled to the drape 122 to provide fluid access to the manifold 120. Another attachment device (not shown) similar to the attachment device 130 may be used to hold the reduced-pressure interface 132 against the drape 122. The first conduit 112, the canister 110, and the second conduit 114 fluidly couples the reduced-pressure treatment unit 108 and the reduced-pressure interface 132. The reduced-pressure interface 132 allows the reduced pressure to be delivered to the tissue site 102. While the amount and nature of reduced pressure applied to a tissue site will typically vary according to the application, the reduced pressure will typically be between −5 mm Hg (−667 Pa) and −500 mm Hg (−66.7 kPa) and more typically between −75 mm Hg (−9.9 kPa) and −300 mm Hg (−39.9 kPa).

The first and second conduits 112, 114 may be single lumen conduits, multi-lumen conduits, or a combination of a single lumen and multi-lumen conduit. In the instance either or both the first and second conduits 112, 114 are a multi-lumen conduit, one lumen may be a primary lumen and another lumen may be a sensing lumen for sensing the level of reduced pressure being applied to the tissue site 102. Liquids or exudates communicated from the manifold 120 through the first conduit 112 are removed from the first conduit 112 and retained within the canister 110.

The reduced-pressure treatment unit 108 includes a reduced-pressure source 134, and may further include an instrumentation unit 136. In an illustrative embodiment, the reduced-pressure source 134 is an electrically-driven vacuum pump. In another implementation, the reduced-pressure source 134 may instead be a manually-actuated or manually-charged pump that does not require electrical power. The reduced-pressure source 134 instead may be any other type of reduced pressure pump, or alternatively a wall suction port such as those available in hospitals and other medical facilities. The reduced-pressure source 134 may be housed within or used in conjunction with the reduced-pressure treatment unit 108, which may also include the instrumentation unit 136. The instrumentation unit 136 may include sensors, processing units, alarm indicators, memory, databases, software, display units, and user interfaces that further facilitate the application of reduced pressure treatment to the tissue site 102. In one example, pressure-detection sensors (not shown) may be disposed at or near the reduced-pressure source 134. The pressure-detection sensors may receive pressure data from the reduced-pressure interface 132 via lumens in the conduits 112, 114 that are dedicated to delivering reduced pressure data to the pressure-detection sensors. The pressure-detection sensors may communicate with a processing unit that monitors and controls the pressure that is delivered by the reduced-pressure source 134.

Referring now primarily to FIGS. 2-6, the canister 110 shown in the system 100 of FIG. 1 is presented in more detail. The canister 110 may be referred to as an in-line canister since the canister 110 is positioned between the first and second conduits 112, 114 that fluidly connect the reduced-pressure dressing 106 and the reduced-pressure treatment unit 108. The canister 110 includes a center body 138, a first end cap 140, and a second end cap 142. The canister 110 is configured to create a continuous, tortuous flow path represented by arrows 157. The continuous, tortuous flow path is a unidirectional flow path.

The center body 138 includes a first end 144 and a second, opposing end 146. A number of fluidly separate body conduits 148 extend from the first end 144 to the second end 146. The number of fluidly separate body conduits 148 may be an uneven number. For example, the number of fluidly separate body conduits 148 may be 3, 5, 7, or more. As shown, the number of fluidly separate body conduits 148 is seven. The number may depend on the desired length of the continuous, tortuous flow path. In a specific example, the center body 138 may have a width, W, of approximately several inches, and more specifically, approximately 3 inches in some embodiments. The center body 138 may also have a length, L, between the first end and the second end 144, 146 of several inches in some embodiments. In more particular embodiments, the length L is approximately 6 inches. Each of the number of fluidly separate body conduits 148 may have a diameter, d, or a width that allows for an approximate canister 110 volumetric size of 170 cc. For example, in some embodiments, the diameter d is approximately 0.375 inches. It should be understood however, the width, W, and length, L, of the center body 138, the number of body conduits 148 contained within the center body 138, and the diameter, d, or width of the body conduits 148 may be adjusted according to the desired volumetric size of the canister 110.

The center body 138 is shown as having an oblong shape with a first side 150 and a second, opposing side 152 that is both substantially planar and substantially parallel. It should be understood that while the center body 138 is shown as having an oblong shape with two sides that are substantially planar and parallel, the oblong shape is but one illustrative embodiment. The center body 138 may take a number of shapes. For example, the center body 138 may be rectangular, square, or cylindrical. A top 154 and a bottom 156 of the center body 138 may be rounded. Each of the number of fluidly separate body conduits 148 may be bonded together to form the center body 138. In one embodiment, each of the number of fluidly separate body conduits 148 are bonded together in a single column. In another embodiment, the number of fluidly separate body conduits 148 are arranged in one or more columns or rows. In yet another embodiment, the center body 138 is a single extruded piece. The center body 138 may be formed of silicone or polyurethane, for example. The center body 138 may be made of a flexible material to make the center body less noticeable and more comfortable if worn under clothing.

The center body 138 may include an absorbent material (not shown) positioned within one or more of the number of fluidly separate body conduits 148. The absorbent material may be one of a hydrophilic foam, a hydrophilic paper, a hydrophilic powder, or a sodium polyacrylate material.

The canister 110 further includes the first end cap 140. The first end cap 140 is connected to the first end 144 of the center body 138. The first end cap 140 may be connected to the center body 138 by a connecting means such as an adhesive bond or a weld bond. The connecting means creates a fluid seal between the first end cap 140 and the center body 138. The first end cap 140 may be formed as a single piece. The first end cap 140 may further be formed of silicone.

The first end cap 140 has a number of return conduits 158 configured to fluidly connect one of the body conduits 148 with another of the body conduits 148. In one embodiment, the return conduits 158 connect two of the number of body conduits 148 that are adjacent. The return conduits 158 may function as turnabouts that redirect fluid received from one conduit into another conduit. The return conduits 158 may redirect fluid into an opposite direction. The first end cap 140 may include a number of protrusions (not shown) corresponding to the return conduits 158. The number of protrusions would be insertable into the corresponding body conduits 148.

The first end cap 140 has a port 160 for receiving an inlet conduit, such as the first conduit 112, that is in fluid communication with the tissue site 102. The first conduit 112 may be connected to the port 160 by a connecting means such as an adhesive bond or a weld bond. The connecting means creates a fluid seal between the first conduit 112 and the port 160. The port 160 is aligned with a first body conduit 170 of the number of body conduits 148 to facilitate fluid communication between the first conduit 112 and the first body conduit 170 of the number of body conduits 148.

The canister 110 further includes the second end cap 142. The second end cap 142 is connected to the second end 146 of the center body 138. The second end cap 142 may be connected to the center body 138 by a connecting means such as an adhesive bond or a weld bond. The connecting means creates a fluid seal between the second end cap 142 and the center body 138. The second end cap 142 may be formed as a single piece. The second end cap 142 may further be formed of silicone.

The second end cap 142 has a number of return conduits 164 configured to fluidly connect one of the body conduits 148 with another of the body conduits 148. In one embodiment, the return conduits 164 connect two of the number of body conduits 148 that are adjacent. The return conduits 164 may function as turnabouts that redirect fluid received from one conduit into another conduit. The return conduits 164 may redirect fluid into an opposite direction. The second end cap 142 may include a number of protrusions (not shown) corresponding to the return conduits 164. The number of protrusions would be insertable into the corresponding body conduits 148.

The second end cap 142 has a port 166 for receiving an outlet conduit, such as the second conduit 114, that is in fluid communication with the reduced-pressure treatment unit 108 and, in particular, the reduced-pressure source 134. The second conduit 114 may be connected to the port 166 by a connecting means such as an adhesive bond or a weld bond. The connecting means creates a fluid seal between the second conduit 114 and the port 166. The port 166 is aligned with an end conduit 194 of the number of body conduits 148 to facilitate fluid communication between the second conduit 114 and the end conduit 194 of the number of body conduits 148. A hydrophobic filter (not shown) may be placed in the second end cap 142, adjacent the port 166, to prevent exudates from exiting the canister 110.

In operation, reduced pressure is supplied to the tissue site 102 by the reduced-pressure treatment unit 108. The canister 110 is a part of the system 100 that communicates the reduced pressure from the reduced-pressure treatment unit 108 to the tissue site 102. While applying reduced pressure to the tissue site 102, fluids, including liquids and exudates, may be removed from the tissue site 102. The liquids and exudates removed from the tissue site 102 are collected and stored in the canister 110. The fluid connection between the body conduits 148 and the return conduits 158, 164 of the first and second end caps creates a continuous, tortuous flow path that is represented by the arrows 157. The continuous, tortuous flow path represented by the arrows 157 is a unidirectional flow path beginning at the port 160 in the first end cap 140 and ending at the port 166 in the second end cap 142. The continuous, tortuous flow path passes through the each of the number of fluidly separate body conduits 148.

Figure 6:
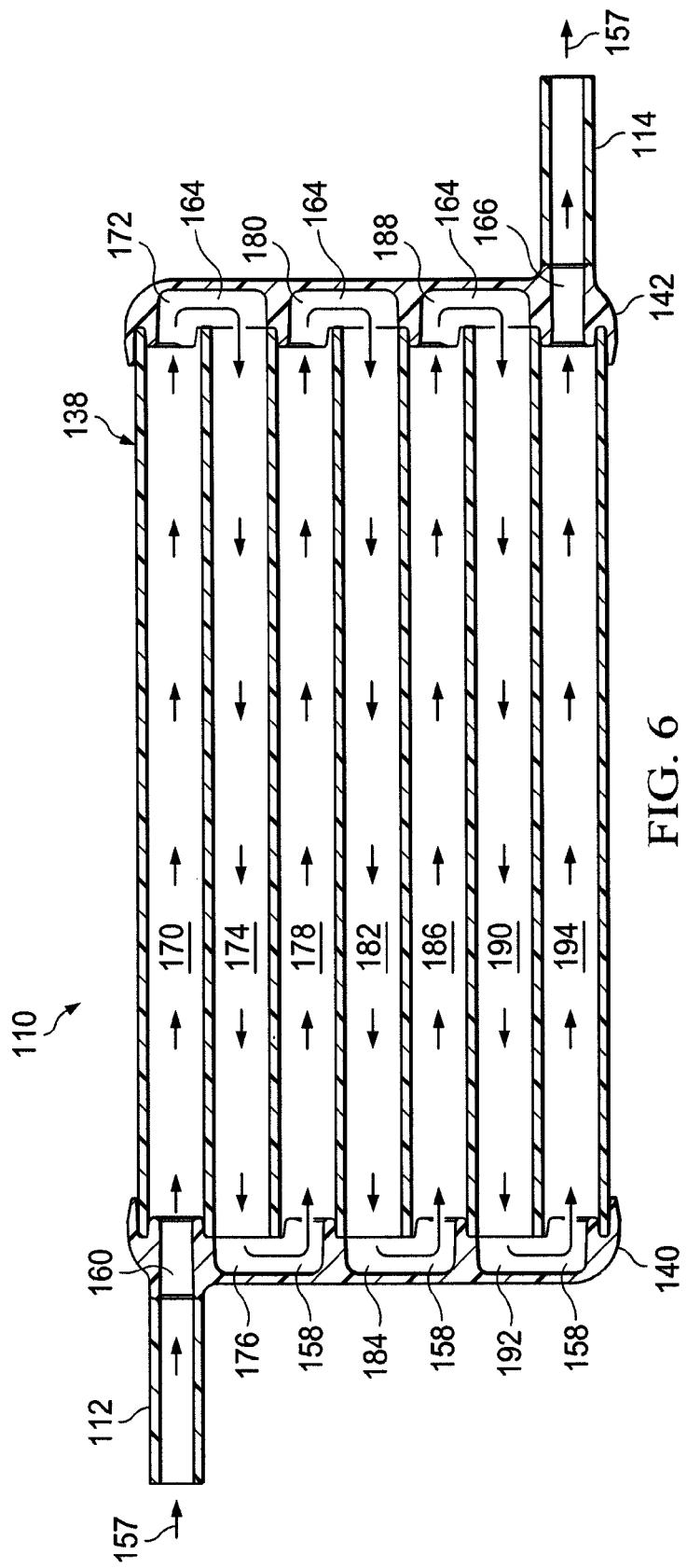
FIG. 6 illustrates a cross-sectional side view of the canister of FIG. 2.
Figure 7:
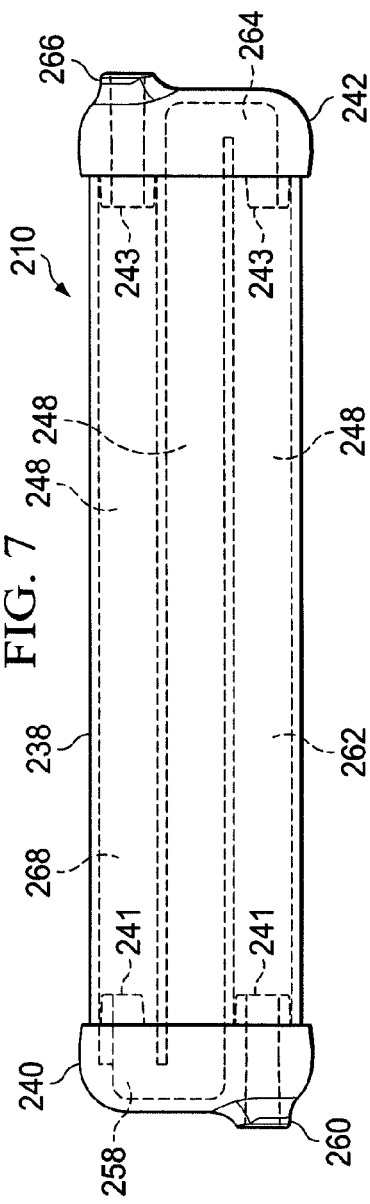
FIG. 7 illustrates a side view of another illustrative embodiment of a canister for use in the system shown in FIG. 1.
Figure 8:
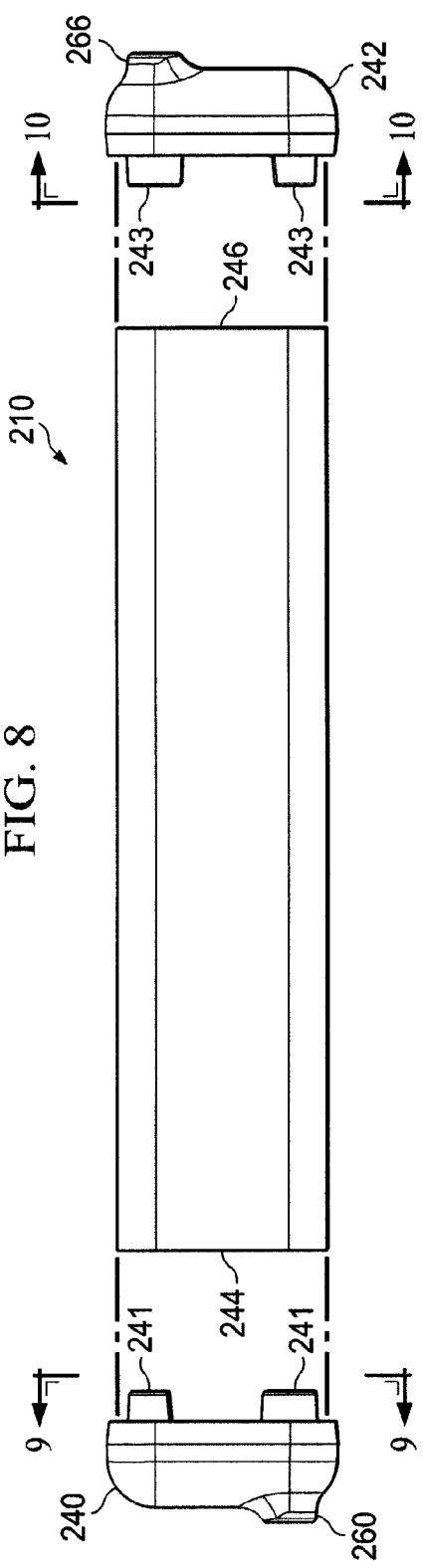
FIG. 8 illustrates an exploded side view of the canister shown in FIG. 7.
Figure 10:
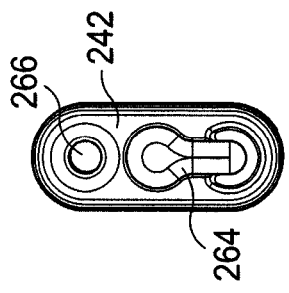
FIG. 10 illustrates a back view of a second end cap of the canister shown in FIG. 7 taken along line 10-10.
Figure 9:
FIG. 9 illustrates a front view of a first end cap of the canister shown in FIG. 7 taken along line 9-9.
Figure 11:
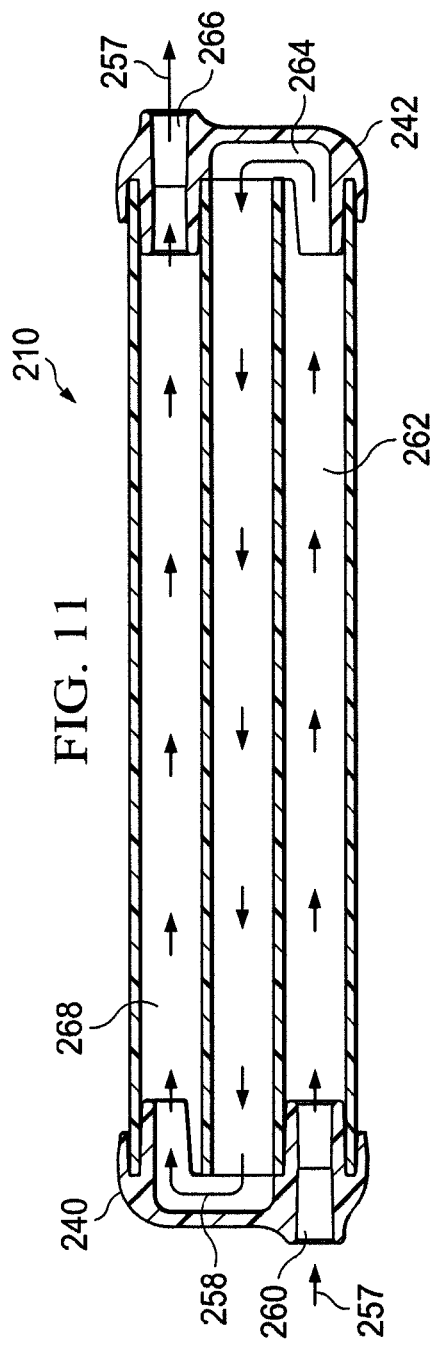
FIG. 11 illustrates a cross-sectional side view of the canister shown in FIG. 7.

Referring now primarily to FIG. 6, but also with reference to FIGS. 2-5, the number of body conduits 148 as shown is seven. The fluids removed from the tissue site 102 enter the canister 110 through the port 160 in the first end cap 140. The fluids are delivered through the port 160 and into a first body conduit 170 of the number of body conduits 148. The fluids may then flow through the first body conduit 170 to a first return conduit 172, positioned in the second end cap 142, and into a second body conduit 174. The fluid from the second body conduit 174 may then flow into a second return conduit 176, positioned in the first end cap 140, and to a third body conduit 178. The fluid from the third body conduit 178 may then flow into a third return conduit 180, positioned in the second end cap 142, and to a fourth body conduit 182. The fluid from the fourth body conduit 182 may then flow into a fourth return conduit 184, positioned in the first end cap 140, and to a fifth body conduit 186. The fluid from the fifth body conduit 186 may then flow into a fifth return conduit 188, positioned in the second end cap 142, and to a sixth body conduit 190. The fluid from the sixth body conduit 190 may then flow into a sixth return conduit 192, positioned in the first end cap 140, and to a seventh body conduit 194. Air and gases may pass through the port 166 positioned in the second end cap 142. However, liquids and exudate will be trapped within the canister 110. As used herein, "fluids" may include liquids, exudate, air, and other gases.

Referring now primarily to FIGS. 7-11, another illustrative embodiment of a canister 210 for use in a reduced-pressure treatment system such as the system 100 of FIG. 1 is presented. The canister 210 is similar to the canister 110 shown in FIGS. 1-6 except (i) the canister 210 includes three fluidly isolated body conduits 248 and (ii) a first end cap 240 and a second end cap 242 include protrusions 241, 243, respectively. The canister 210 may be used for tissue sites that produce low volume exudates.

The canister 210 is positioned between the first and second conduits 112, 114 of FIG. 1. The canister 210 includes a center body 238, the first end cap 240, and the second end cap 242. The canister 210 is configured to create a continuous, tortuous flow path represented by arrows 257. The continuous, tortuous flow path is a unidirectional flow path.

The center body 238 includes a first end 244 and a second, opposing end 246. The number of fluidly separate body conduits 248 extend from the first end 244 to the second end 246. As shown, the number of fluidly separate body conduits 248 is three. The center body 238 may include an absorbent material (not shown) positioned within one or more of the number of fluidly separate body conduits 248. The absorbent material may be one of a hydrophilic foam, a hydrophilic paper or a hydrophilic powder.

The first end cap 240 is connected to the first end 244 of the center body 238. The first end cap 240 may be connected to the center body 238 by a connecting means such as an adhesive bond or a weld bond. The first end cap 240 may be formed as a single piece and may further be formed of silicone.

The first end cap 240 has a return conduit 258 configured to fluidly connect one of the body conduits 248 with another of the body conduits 248. In one embodiment, the return conduit 258 connects two of the number of body conduits 248 that are adjacent. The return conduit 258 may function as a turnabout that redirects fluid received from one conduit into another conduit. The return conduit 258 may redirect fluid into an opposite direction. The first end cap 240 may include a number of protrusions 241 corresponding to the return conduit 258. The number of protrusions 241 are configured to be inserted into the corresponding body conduits 248.

The first end cap 240 has a port 260 for receiving an inlet conduit, such as the first conduit 112, that is in fluid communication with the tissue site 102. The port 260 is aligned with a first body conduit 262 of the number of body conduits 248 to facilitate fluid communication between the first conduit 112 and the first body conduit 262 of the number of body conduits 248.

The second end cap 242 is connected to the second end 246 of the center body 238. The second end cap 242 may be connected to the center body 238 by a connecting means such as an adhesive bond or a weld bond. The second end cap 242 may be formed as a single piece and may further be formed of silicone.

The second end cap 242 has a return conduit 264 configured to fluidly connect one of the body conduits 248 with another of the body conduits 248. In one embodiment, the return conduit 264 connects two of the number of body conduits 248 that are adjacent. The return conduit 264 may function as a turnabout that redirects fluid received from one conduit into another conduit. The return conduit 264 may redirect fluid into an opposite direction. The second end cap 242 may include a number of protrusions 243 corresponding to the return conduit 264. The number of protrusions 243 are configured to be inserted into the corresponding body conduits 248.

The second end cap 242 has a port 266 for receiving an outlet conduit, such as the second conduit 114, that is in fluid communication with the reduced-pressure treatment unit 108 and, in particular, the reduced-pressure source 134 of FIG. 1. The port 266 is aligned with an end conduit 268 of the number of body conduits 248 to facilitate fluid communication between the second conduit 114 and the end conduit 268 of the number of body conduits 248. A hydrophobic filter (not shown) may be placed in the second end cap 242, adjacent the port 266, to prevent exudates from exiting the canister 210.

Figure 12A:
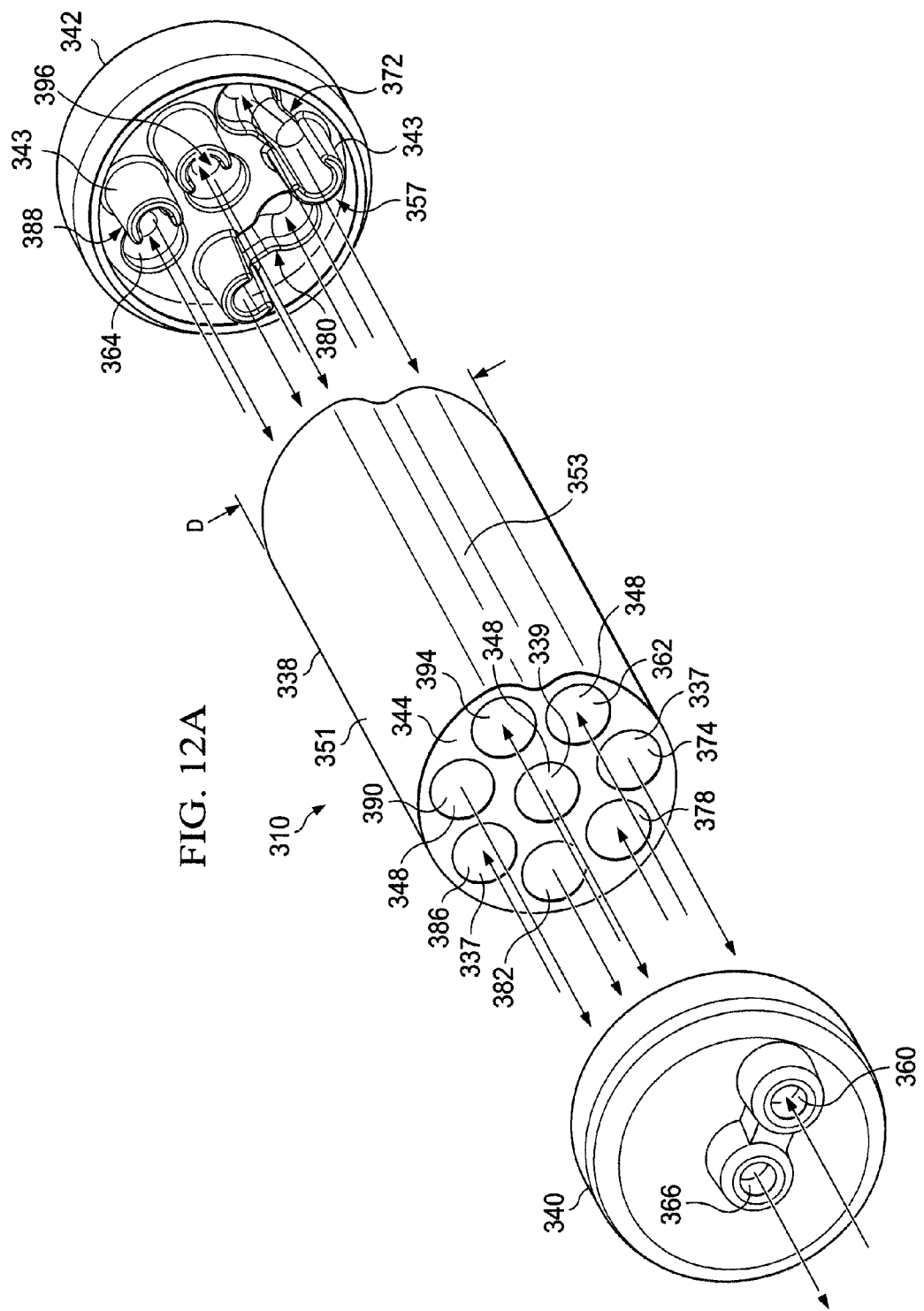
FIGS. 12A and 12B illustrate a perspective view of another illustrative embodiment of a canister for use in the system shown in FIG. 1.
Figure 12B:
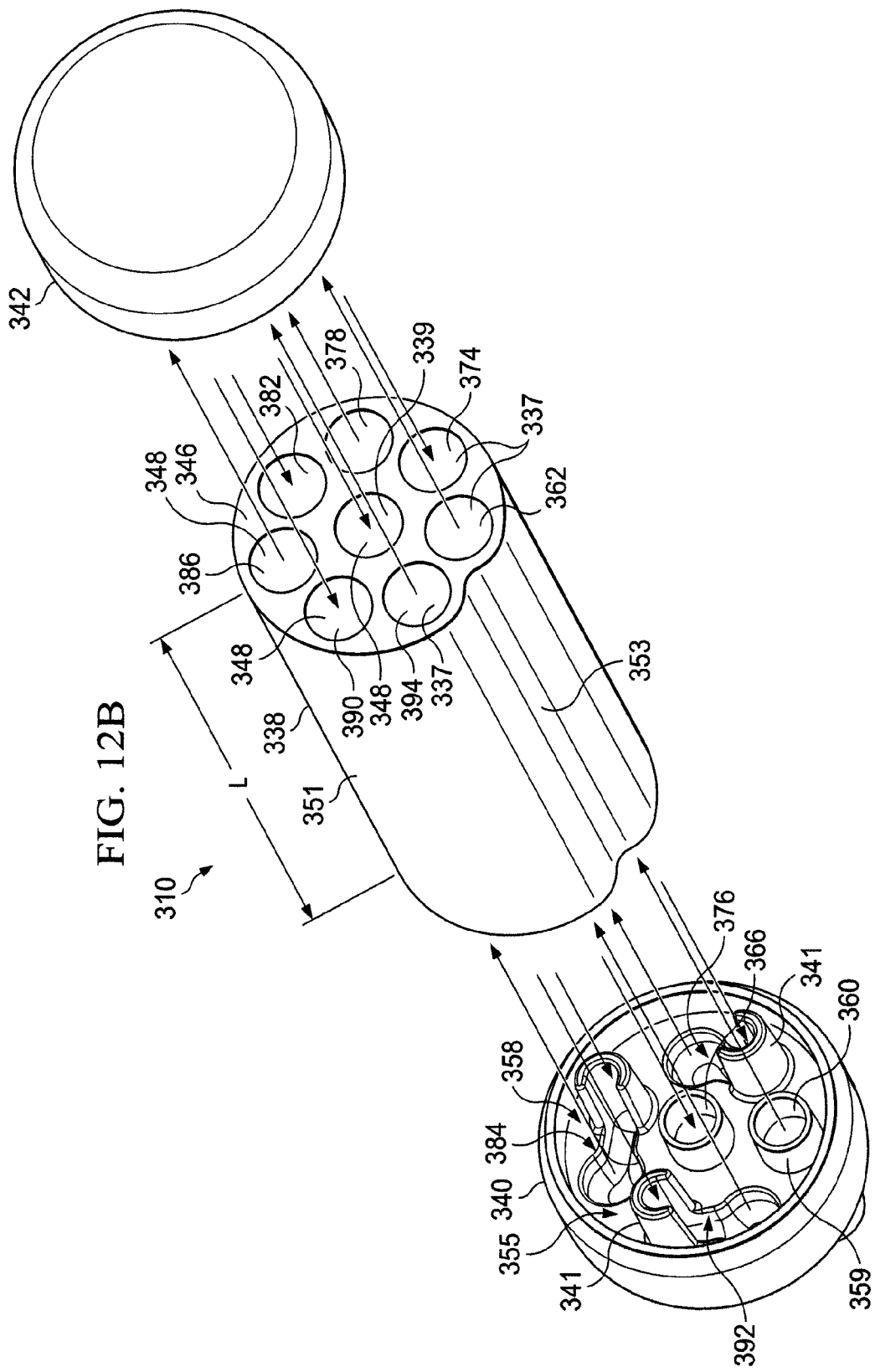

Referring now primarily to FIGS. 12A and 12B, another illustrative embodiment of a canister 310 for use in a reduced-pressure treatment system such as the system 100 of FIG. 1 is presented. The canister 310 may be referred to as an in-line canister since the canister 310 is connected to the first and second conduits 112, 114 shown in FIG. 1 that fluidly connect the reduced-pressure dressing 106 and the reduced-pressure treatment unit 108. The canister 310 includes a center body 338, a first end cap 340, and a second end cap 342. The canister 310 has a cylindrical shape. The canister 310 is configured to create a continuous, tortuous flow path. The continuous, tortuous flow path is a unidirectional flow path.

The center body 338 includes a first end 344 and a second, opposing end 346. A number of fluidly separate body conduits 348 extend from the first end 344 to the second end 346. The number of fluidly separate body conduits 348 may be an even or an uneven number. For example, the number of body conduits may be 8. The number may depend on the desired length of the continuous, tortuous flow path. The center body 338 may have a diameter, D, of approximately 1-2 inches in some embodiments. In more particular embodiments, the diameter D may be approximately 1.6 inches. The center body 338 may also have a length, L, between the first end and the second end 344, 346 of several inches in some embodiments, and approximately 4 inches in more particular embodiments. Each of the number of fluidly separate body conduits 348 may have a diameter, d, or a width of which allow for an approximate volumetric size of 130 cc. It should be understood however, the diameter, D, and length, L, of the center body 338, the number of body conduits 348 contained within the center body 338, and the diameter, d, or width of the body conduits 348 may be adjusted according to the desired volumetric size of the canister 310.

The center body 338 is shown as having a cylindrical shape. The center body 338 includes an outer surface 351. The outer surface 351 of the center body 338 may include a groove 353 that extends along the longitudinal axis, or the length, L, of the center body 338. The groove 353 may be used during the manufacturing process to properly align the number of fluidly separate body conduits 348 within the center body 338. The number of fluidly separate body conduits 348 may include a center conduit 339 and a number of outer body conduits 337 that are radially positioned around the center conduit 339. The center body 338 may be a single extruded piece and may be formed of silicone.

The center body 338 may include an absorbent material (not shown) positioned within one or more of the number of fluidly separate body conduits 348. The absorbent material may be one of a hydrophilic foam, a hydrophilic paper or a hydrophilic powder.

The canister 310 further includes the first end cap 340. The first end cap 340 is connected to the first end 344 of the center body 338. The first end cap 340 may be connected to the center body 338 by a connecting means such as an adhesive bond or a weld bond. The connecting means creates a fluid seal between the first end cap 340 and the center body 338. The first end cap 340 may be formed as a single piece. The first end cap 340 may further be formed of silicone.

The first end cap 340 includes a first plenum 355 for receiving fluids. The first plenum 355 may have a number of return conduits 358 positioned within the first plenum 355.

The return conduits 358 are configured to fluidly connect one of the body conduits 348 with another of the body conduits 348. The return conduits 358 may function as turnabouts that redirect fluid received from one conduit into another conduit. The return conduits 358 may redirect fluid into an opposite direction. The first end cap 340 may include a number of protrusions 341 corresponding to the return conduits 358. The number of protrusions 341 are configured to be insertable into the corresponding body conduits 348.

The first end cap 340 has an inlet port 360 for receiving an inlet conduit, such as the first conduit 112, and an outlet port 366 for receiving an outlet conduit, such as the second conduit 114. The inlet conduit, or the first conduit 112, is in fluid communication with the tissue site 102, and the outlet conduit, or the second conduit 114, is in fluid communication with the reduced-pressure source 134. The first conduit 112 may be connected to the inlet port 360 and the second conduit 114 may be connected to the outlet port 366 by a connecting means such as an adhesive bond or a weld bond. The connecting means creates a fluid seal between the first conduit 112 and the inlet port 360 and the second conduit 114 and the outlet port 366. The inlet port 360 is aligned with one of the number of body conduits 348. In one embodiment, the inlet port 360 is aligned with one of the number of outer body conduits 337 such as a first body conduit 362. In another embodiment, the inlet port is aligned with the center conduit 339. The inlet port 360 aligns with one of the number of body conduits 348 to facilitate fluid communication between the first conduit 112 and the one of the number of body conduits 348. The inlet port 360 may include a protrusion 359 for inserting into the one of the number of body conduits 348. The outlet port 366 is aligned with another of the number of body conduits 348. In one embodiment, the outlet port 366 is aligned with the center conduit 339. In another embodiment, the outlet port 366 is aligned with one of the radial body conduits such as the first body conduit 362. The outlet port 366 aligns with another of the number of body conduits 348 to facilitate fluid communication between the second conduit 114 and the another of the number of body conduits 348. A hydrophobic filter (not shown) may be placed in the first end cap 340, adjacent the outlet port 366, to prevent exudates from exiting the canister 310.

The canister 310 further includes the second end cap 342. The second end cap 342 is connected to the second end 346 of the center body 338. The second end cap 342 may be connected to the center body 338 by a connecting means such as an adhesive bond or a weld bond. The connecting means creates a fluid seal between the second end cap 342 and the center body 338. The second end cap 342 may be formed as a single piece. The second end cap 342 may further be formed of silicone.

The second end cap 342 includes a second plenum 357 for receiving fluids. The second end cap 342 has a number of return conduits 364 positioned within the second plenum 357. The return conduits 364 are configured to fluidly connect one of the body conduits 348 with another of the body conduits 348. The return conduits 364 may function as turnabouts that redirect fluid received from one body conduit into another body conduit. The return conduits 364 may redirect fluid into an opposite direction. The second end cap 342 may include a number of protrusions 343 corresponding to the return conduits 364. The number of protrusions would be insertable into the corresponding body conduits 348.

In operation, reduced pressure is supplied to the tissue site 102 by the reduced-pressure treatment unit 108. The canister 310 is a part of the system 100 that communicates the reduced pressure from the reduced-pressure treatment unit 108 to the tissue site 102. While applying reduced pressure to the tissue site 102, fluids, including liquids and exudates, may be removed from the tissue site 102. The liquids and exudates removed from the tissue site 102 are collected and stored in the canister 310. The fluid connection between the body conduits 348 and the return conduits 358, 364 of the first and second end caps creates a continuous, tortuous flow path. The continuous, tortuous flow path is a unidirectional flow path beginning at the inlet port 360 in the first end cap 340 and ending at the outlet port 366 in the first end cap 340. The continuous, tortuous flow path passes through the each of the number of fluidly separate body conduits 348.

In one illustrative, non-limiting embodiment, the fluids removed from the tissue site 102 enter the canister 310 through the inlet port 360 in the first end cap 340. The fluids are delivered through the inlet port 360 and into a first body conduit 362 of the number of body conduits 348. The fluids may then flow through the first body conduit 362 to a first return conduit 372, positioned in the second end cap 342, into a second body conduit 374. The fluid from the second body conduit 374 may then flow into a second return conduit 376, positioned in the first end cap 340, to a third body conduit 378. The fluid from the third body conduit 378 may then flow into a third return conduit 380, positioned in the second end cap 342, to a fourth body conduit 382. The fluid from the fourth body conduit 382 may then flow into a fourth return conduit 384, positioned in the first end cap 340, to a fifth body conduit 386. The fluid from the fifth body conduit 386 may then flow into a fifth return conduit 388, positioned in the second end cap 342, to a sixth body conduit 390. The fluid from the sixth body conduit 390 may then flow into a sixth return conduit 392, positioned in the first end cap 340, to a seventh body conduit 394. The fluid from the seventh body conduit 394 may then flow into a seventh return conduit or end conduit 396 positioned in the second end cap 342, to the center conduit 339. Air and gases may pass through the outlet port 366 positioned in the first end cap 340. However, liquids and exudate will be trapped within the canister 310. In this embodiment, fluid received by the inlet port 360 travels through each of the outer body conduits 337 prior to reaching the center conduit 339 and traveling towards the outlet port 366.

Figure 13A:
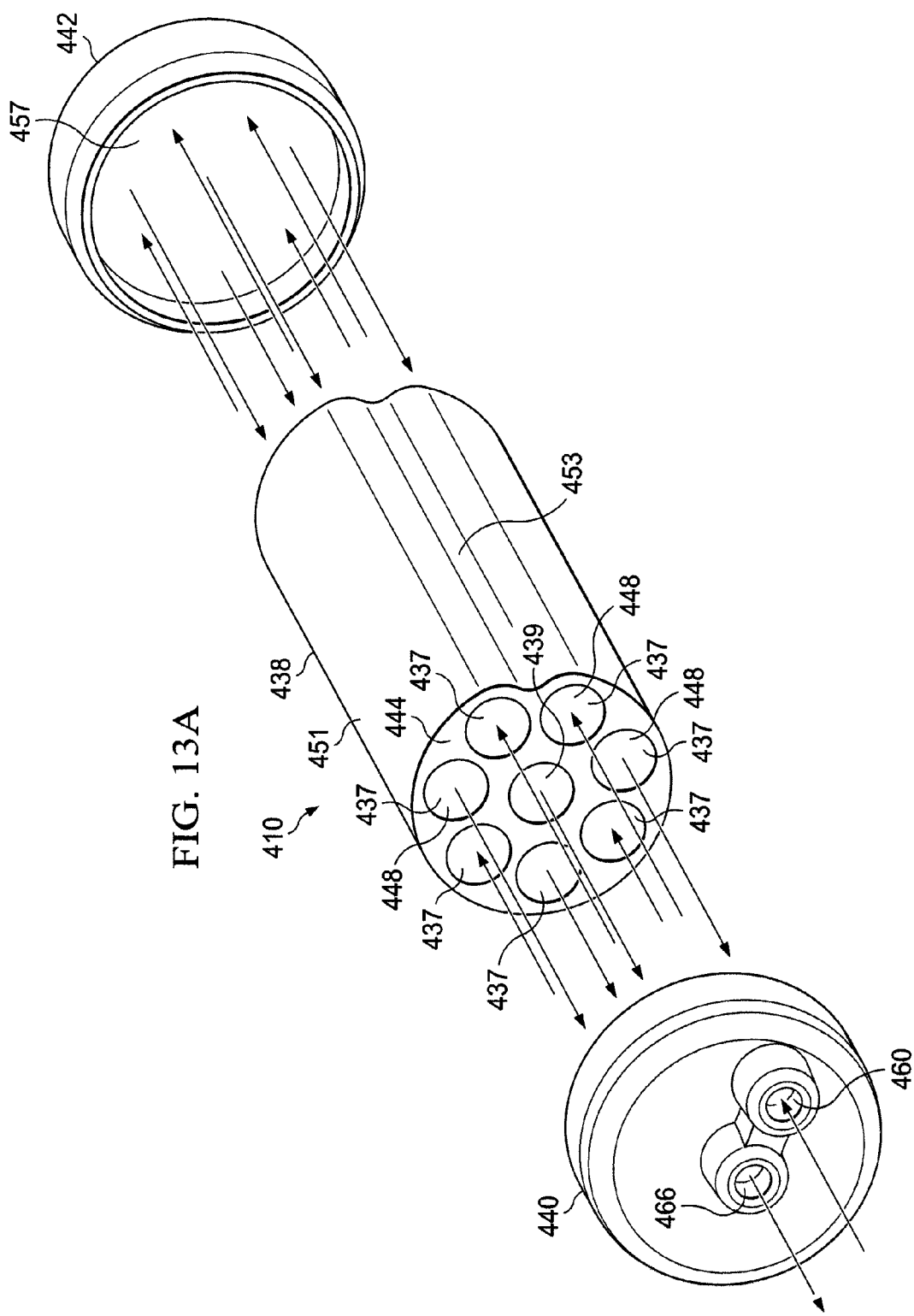
FIGS. 13A and 13B illustrate a perspective view of another illustrative embodiment of a canister for use in the system shown in FIG. 1.
Figure 13B:
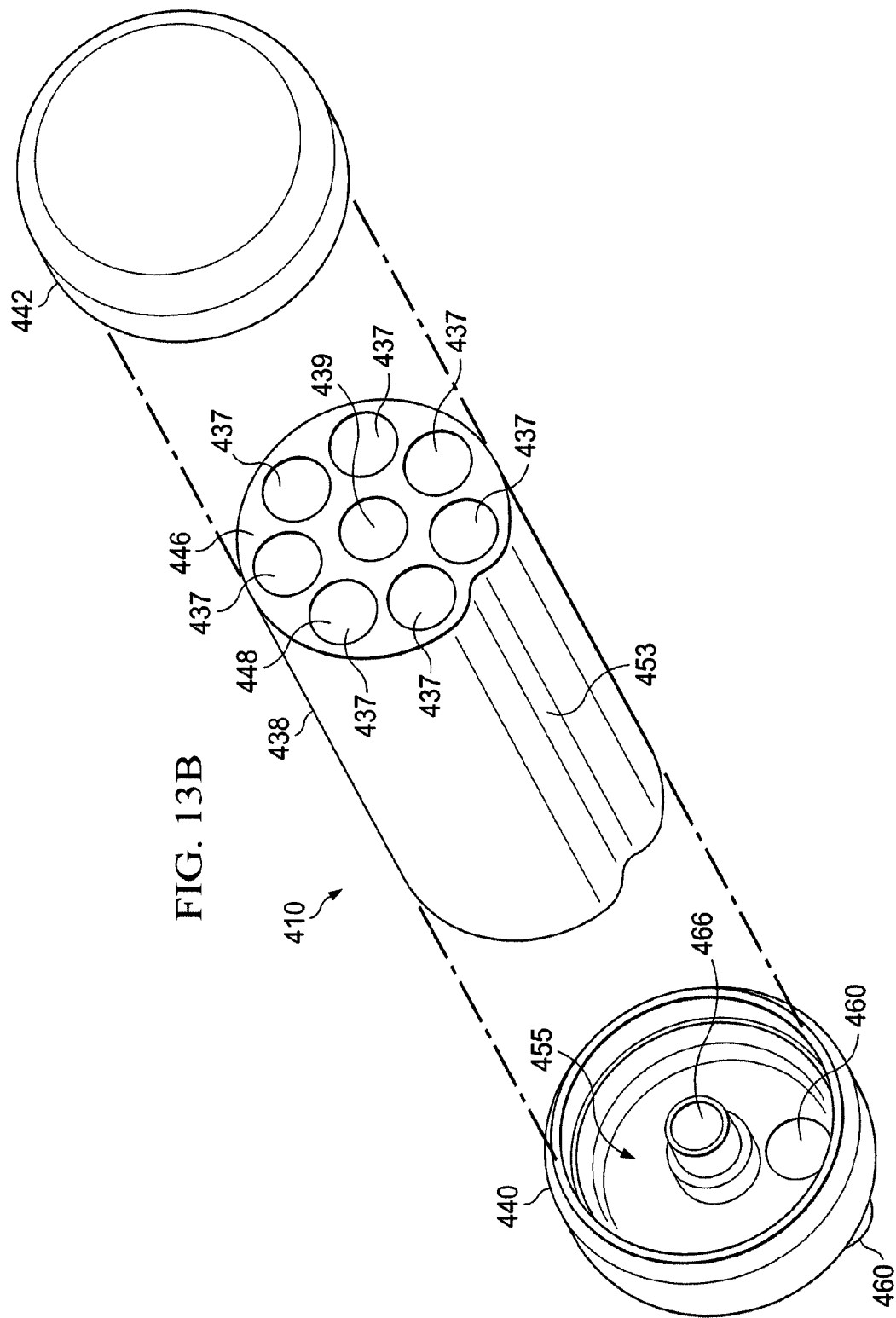

Referring now primarily to FIGS. 13A and 13B, another illustrative embodiment of a canister 410 for use in a reduced-pressure treatment system such as the system 100 of FIG. 1 is presented. The canister 410 is similar to the canister 310 shown in FIGS. 12A and 12B except a first and second end cap 440, 442 do not include return conduits.

The canister 410 includes a center body 438, a first end cap 440, and a second end cap 442. The canister 410 has a cylindrical shape and is configured to create a tortuous flow path. The center body 438 includes a first end 444 and a second, opposing end 446. A number of fluidly separate body conduits 448 extend from the first end 444 to the second end 446. The center body 438 includes an outer surface 451. The outer surface 451 of the center body 438 may include a groove 453 that extends along the longitudinal axis, or the length of the center body 438. The number of fluidly separate body conduits 448 may include a center body conduit 439 and a number of outer body conduits 437 that are radially positioned around the center body conduit 439. The center body 438 may be a single extruded piece and may be formed of silicone.

The center body 438 may include an absorbent material (not shown) positioned within one or more of the number of fluidly separate body conduits 448. The absorbent material may be one of a hydrophilic foam, a hydrophilic paper or a hydrophilic powder.

The canister 410 further includes the first end cap 440. The first end cap 440 is connected to the first end 444 of the center body 438. The first end cap 440 may be connected to the center body 438 by a connecting means such as an adhesive bond or a weld bond. The first end cap 440 may be formed as a single piece and may further be formed of silicone.

The first end cap 440 includes a first plenum 455 for receiving fluids. The first end cap 440 has an inlet port 460 for receiving an inlet conduit, such as the first conduit 112, and an outlet port 466 for receiving an outlet conduit, such as the second conduit 114. The inlet conduit, or the first conduit 112, is in fluid communication with the tissue site 102, and the outlet conduit, or the second conduit 114, is in fluid communication with the reduced-pressure source 134. The first conduit 112 may be connected to the inlet port 460 and the second conduit 114 may be connected to the outlet port 466 by a connecting means such as an adhesive bond or a weld bond. In one embodiment, the inlet port 460 is in fluid communication with all but one of the number of body conduits 448. For example, the inlet port 460 may be in fluid communication with the outer body conduits 437. In this example, the outlet port 466 is in fluid communication with the center body conduit 439. The outlet port 466 may include a protrusion configured to be positioned within the center body conduit 439. The first plenum 455 is an open space or cavity. Fluids received by the inlet port 460 enter the first plenum 455 and are distributed to the outer body conduits 437. The fluids pass through the outer body conduits 437 and enter the second end cap 442 having a second plenum 457.

The second end cap 442 is connected to the second end 446 of the center body 438. The second end cap 442 may be connected to the center body 438 by a connecting means such as an adhesive bond or a weld bond. The second end cap 442 may be formed as a single piece and may further be formed of silicone. The second end cap 442 includes the second plenum 457 for receiving fluids. The second plenum 457 is an open space or cavity that receives fluids from one or more of the number of body conduits 448 in fluid communication with the inlet port 460 such as the outer body conduits 437. Fluid received by the second plenum 457 is directed into the center body conduit 439 and to the outlet port 466. Fluid in the second plenum 457 may be directed into the center body conduit 439 by means of reduced pressure.

In another embodiment (not shown), the inlet port 460 is fluidly connected with one of the number of body conduits 448. The inlet port 460 aligns with one of the number of body conduits 448 to facilitate fluid communication between the first conduit 112 and the one of the number of body conduits 448. The inlet port 460 may include a protrusion for inserting into the one of the number of body conduits 448. The outlet port 466 is aligned with the other conduits of the number of body conduits 448.

In operation, reduced pressure is supplied to the tissue site 102 by the reduced-pressure treatment unit 108. The canister 410 is a part of the system 100 that communicates the reduced pressure from the reduced-pressure treatment unit 108 to the tissue site 102. While applying reduced pressure to the tissue site 102, fluids, including liquids and exudates, may be removed from the tissue site 102. The liquids and exudates removed from the tissue site 102 are collected and stored in the canister 410. The fluid connection between the body conduits 448 and the first and second end caps 440, 442 creates a tortuous flow path having several parallel paths. The tortuous flow path begins at the inlet port 460 in the first end cap 440 and ends at the outlet port 466 in the first end cap 440. The tortuous flow path passes through each of the number of body conduits 448.

In one illustrative, non-limiting embodiment, the fluids removed from the tissue site 102 enter the canister 410 through the inlet port 460 in the first end cap 440. The fluids are delivered through the inlet port 460 into the first plenum 455. The fluid is then directed to any one of the outer body conduits 437. The fluid is received by the second plenum 457 and directed into the center body conduit 439.

It should be apparent from the foregoing that an invention having significant advantages has been provided. While the invention is shown in only a few of its forms, it is not just limited but is susceptible to various changes and modifications without departing from the spirit thereof.

We claim:

1. A canister for use in administering reduced pressure to a tissue site, the canister comprising:
    a center body comprising a first end, a second end, a first body conduit, and a second body conduit fluidly separated from the first body conduit, the first body conduit and second body conduit extending from the first end to the second end;
    a first end cap connected to the first end of the center body, the first end cap comprising return conduits configured to fluidly connect one of the body conduits with another of the body conduits, the first end cap having a port for receiving a first conduit in fluid communication with the tissue site; and
    a second end cap connected to the second end of the center body, the second end comprising return conduits configured to fluidly connect one of the body conduits with another of the body conduits, the second end cap having a port for receiving a second conduit in fluid communication with a reduced pressure source;
    wherein the fluid connection of the body conduits to the return conduits of the first and second end caps creates a continuous, tortuous flow path.

2. The canister of claim 1, wherein the first body conduit and the second body conduit are radially positioned within the center body.

3. The canister of claim 1, wherein the center body has an oblong shape.

4. The canister of claim 1, wherein a first side and second, opposing side of the center body are planar.

5. The canister of claim 1, wherein the first body conduit and the second body conduit are bonded together to form the center body having a planar shape.

6. The canister of claim 1, wherein:
    the first body conduit and the second body conduit are bonded together to form the center body having a planar shape;
    the continuous, tortuous flow path is a unidirectional flow path beginning at the port in the first end cap and ending at the port in the second end cap; and
    the continuous, tortuous flow path passes through the first body conduit and the second body conduit.

7. The canister of claim 6, further comprising an additional number of fluidly separate body conduits, wherein each of the fluidly separate body conduits are positioned adjacent to another of the fluidly separate body conduits to form a single column of conduits.

8. The canister of claim 1, further comprising an additional number of fluidly separate body conduits, wherein the fluidly separate conduits are arranged in one or more columns or rows.

9. The canister of claim 1, further comprising an absorbent material positioned within at least one of the first body conduit and the second body conduit.

10. The canister of claim 9, wherein the absorbent material is one of a hydrophilic foam, a hydrophilic paper or a hydrophilic powder.

11. The canister of claim 7, wherein there are an uneven number of fluidly separate body conduits.

12. The canister of claim 1, further comprising a hydrophobic filter positioned within the second end cap, proximate the port.

13. The canister of claim 1, wherein the canister is formed from silicone.

14. The canister of claim 1, wherein the center body is formed as a single, extruded piece.

15. The canister of claim 1, further comprising:
   an inlet conduit bonded to the port on the first end cap, the inlet conduit for providing fluid communication between the tissue site and the canister; and
   an outlet conduit bonded to the port on the second end cap, the outlet conduit for providing fluid communication between the canister and a reduced pressure source.

16. A system for use in administering reduced pressure to a tissue site, the system comprising:
   a reduced-pressure dressing positioned proximate the tissue site, the reduced-pressure dressing including a manifold positioned within the tissue site for delivering reduced pressure to the tissue site;
   an in-line canister fluidly connected to the reduced-pressure dressing through a first conduit for receiving and storing fluid received from the tissue site, the in-line canister comprising:
      a center body comprising a first end, a second end, a first body conduit, and a second body conduit fluidly separated from the first body conduit, the first body conduit and second body conduit extending from the first end to the second end;
      a first end cap connected to the first end of the center body, the first end cap comprising return conduits configured to fluidly connect one of the body conduits with another of the body conduits, the first end cap having a port for receiving a first conduit in fluid communication with the tissue site; and
      a second end cap connected to the second end of the center body, the second end comprising return conduits configured to fluidly connect one of the body conduits with another of the body conduits, the second end cap having a port for receiving a second conduit in fluid communication with a reduced pressure source;
      wherein the fluid connection of the body conduits to the return conduits of the first and second end caps creates a continuous, tortuous flow; and
   a reduced-pressure treatment unit fluidly connected to the canister through a second conduit, the reduced-pressure treatment unit including a reduced pressure source for providing reduced pressure to the tissue site.

* * * * *